United States Patent [19]

Labaw et al.

[11] Patent Number: 4,705,862

[45] Date of Patent: Nov. 10, 1987

[54] CHEMICAL PROCESSES FOR 2-(2-HALO-3,4-DIMETHOXYBENZYL)-5-(4-METHOXYPHENYL)OXAZOLIDINES

[75] Inventors: Clifford S. Labaw, Philadelphia; Alan W. Tremper, Lansdowne, both of Pa.

[73] Assignee: SmithKline Beckman Corporation, Philadelphia, Pa.

[21] Appl. No.: 909,759

[22] Filed: Sep. 19, 1986

Related U.S. Application Data

[63] Continuation of Ser. No. 657,904, Oct. 5, 1984, abandoned.

[51] Int. Cl.$^4$ .................. C07D 263/06; C07D 223/16
[52] U.S. Cl. ..................................... 548/215; 540/595
[58] Field of Search ........................................... 548/215

[56] References Cited

U.S. PATENT DOCUMENTS 4,197,297  4/1980  Weinstock ........................... 540/595

FOREIGN PATENT DOCUMENTS 1094238  2/1967  United Kingdom .
1595502  8/1981  United Kingdom .

OTHER PUBLICATIONS

Johnson et al., J. Org. Chem., 47 1205 (1982).
Labaw et al., CA 105-60593s.

*Primary Examiner*—Donald G. Daus
*Assistant Examiner*—Cecilia Shen
*Attorney, Agent, or Firm*—Vincent L. Fabiano; Stuart R. Suter; Alan D. Lourie

[57] ABSTRACT

New intermediates, namely 2-(2-halo-3,4-dimethoxybenzyl)-5-(4-methoxyphenyl)-oxazolidines, are prepared by a synthetic sequence which uses a Darzen's reaction in a homogeneous solvent system.

4 Claims, No Drawings

CHEMICAL PROCESSES FOR 2-(2-HALO-3,4-DIMETHOXYBENZYL)-5-(4-METHOXYPHENYL)OXAZOLIDINES

This is a continuation of copending application Ser. No. 657,904 filed Oct. 5, 1984, now abandoned.

This invention relates to new intermediates and processes which are useful for preparing N-[2-hydroxy-2-(4'-methoxyphenyl)ethyl]-2-(2-halo-3,4-dimethoxyphenyl)ethyl amines. The latter compounds are, in turn, chemical intermediates which are known to be useful for preparing certain dopaminergic and anti-hypertensive agents such as fenoldopam, U.K. Pat. No. 1,595,502 or U.S. Pat. No. 4,197,297.

The overall reaction sequence which uses this invention is illustrated as follows:

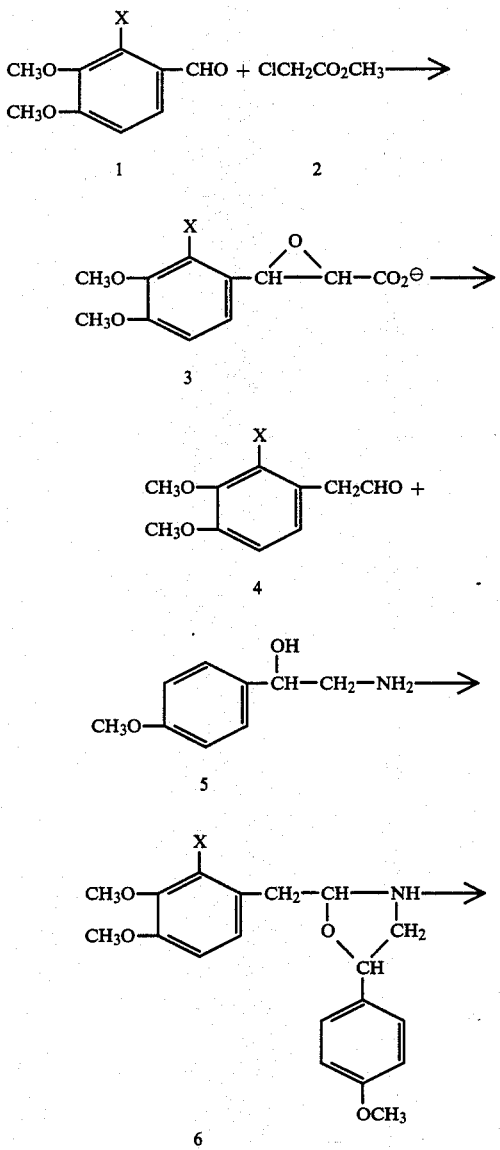

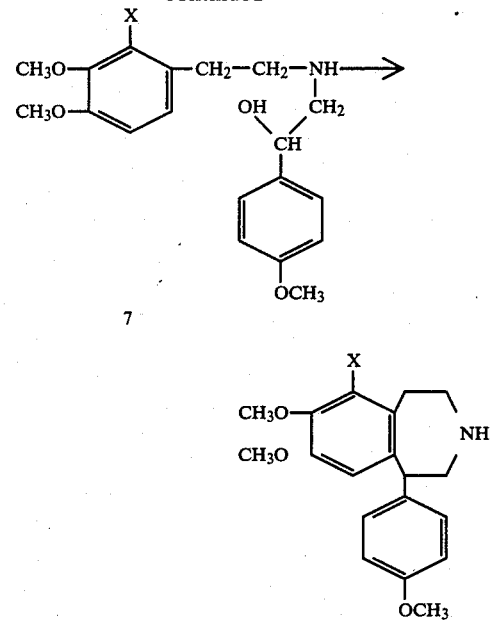

In the reaction sequence above, X is chloro or fluoro.

The Darzen's homologation reaction, as is known to the art, involves reaction of an aldehyde with a α-halo lower alkyl alkanoate in the presence of an acid binding agent, such as an alkali metal lower alkoxide, to give a glycidic acid ester. This ester is, then, saponified, usually with aqueous alkali. The resulting glycidic acid is rearranged, following decarboxylation, in the presence of acid to give the homo aldehyde.

C. R. Johnson et al., J. Org. Chem. 47 1205 (1982), report that the low and uncertain yields of the homo products of the Darzen's reaction may be due to premature hydrolysis of the ester reagent and subsequent formation of a halohydrin by-product. Most often, the reaction conditions of the prior art Darzen's reactions involve a biphase or solid-solvent system, for example U.K. Pat. No. 1,094,238. Either the high cost of chemical or low through-put of the reaction, which are reported for various prior art modifications which have been suggested to improve yields of the Darzen's reaction, precludes commerical use of the reaction in many instances.

The prior art, therefore, reports uncertain, usually low, yields of the desired higher homologous product using the Darzen's reaction.

We have now discovered that, with Darzen's homologation of a 2-halo-3,4-dimethoxybenzaldehyde, good and predictable yields, from 90 to 95%, are obtained using a homogeneous solvent system such as reacting the two starting materials, with an excess of the ester such as methyl chloro- or bromoacetate, in methylene chloride in the presence of a concentrated solution of an alkali metal $C_{1-4}$-alkoxide in a lower alkanol, such as methanol. Temperature is maintained at from $-20°$ to $5°$ C.

The hydrolysis is then carried out at about 20°-25° C. by adding aqueous alkali, such as a concentrated sodium or potassium hydroxide aqueous solution, to the reaction mixture. 50% Sodium hydroxide solution is preferred. The product is the preferred trans sodium salt of the glycidic acid which is produced in situ in quantitative yield to be used for the following decarboxylation. The water-methylene chloride system is taken to pH 5 with acid at 30° C. for two to five hours to rearrange and decarboxylate the glycidic acid in good yield to produce the desired phenylacetaldehyde (4).

The methylene chloride-water mixtures which are necessarily used in the hydrolysis-rearrangement steps tend to form emulsions which make the isolation of the desired phenylacetaldehyde (4) difficult. Unexpectedly, addition of a small quantity of a phase transfer catalyst has solved this problem. For example, between 0.5 to 1.5%, by weight, of catalyst based on the benzaldehyde, is added when ethyl triphenyl phosphonium iodide is the catalyst. Slightly larger quantities, up to 3%, may be necessary when benzyl triphenyl phosphonium chloride, benzyl triethyl ammonium chloride or tetrabutyl phosphonium chloride are used. The Darzen's step on a 12 liter scale starting with 2-chloro3,4-dimethoxybenzaldehyde gave the end product secondary amine (7) in which X is chloro, in 57.5% overall yield with no trace of the added catalyst.

The 2-halo-3,4-dimethoxyphenylacetaldehyde (4) is reacted with a stoichiometric excess of 2-(4'-methoxyphenyl)1-aminoethanol (5) in a lower alkanol at a temperature from the range of −10° to 10°. The temperature of this reaction is not as critical as are others of the reaction sequence described herein but, since the next reaction is carried out at a low temperature, the given range is conveniently used for oxazolidine formation. We have found that the equilibrium of the reaction is displaced toward the oxazolidine when a mole ratio of 1 to 1.4, acetaldehyde/aminoethanol, is used.

The new intermediate of structure 6 is a part of this invention. The 2-(2-halo-3,4-dimethoxybenzyl)-5-(4-methoxyphenyl)-oxazolidine may be optionally isolated but is most often used in situ. The oxazolidine is formed in situ as a mixture of substantially equal quantities of cis and trans isomers which both react in the next step of the reaction. The formation of the oxazolidine intermediate is very quick and complete.

The methanolic reaction mixture which contains the oxazolidine (6) is, then, treated with an excess of an organometallic reducing agent, such as sodium borohydride, at below 10° C. followed by a period of room temperature, to give the desired N-[2-hydroxy-2-(4-methoxyphenyl)ethyl]-2-(2-halo-3,4-dimethoxyphenyl)ethyl amine (7). This product is isolated by methods known to the art and is then cyclized by methods described in the prior art to give a compound of formula 8.

The following examples illustrate the operation of this invention. All temperatures are Centigrade.

EXAMPLE 1

A. General Overall Pilot Procedure:

Step 1. Preparation of 2-chloro-3-hydroxy-4-methoxybenzaldehyde

Chlorine gas is introduced into a solution of 3-hydroxy-4-methoxybenzaldehyde in N,N-dimethylformamide at −10° to −30° C. When the addition of chlorine is complete, the reaction mixture is stirred at −25° C. for 30 minutes and, then, poured into water. The product is separated by filtration and washed with water. The wet product may be dried or used directly in the next step. Average yield, 73%.

Step 2. Preparation of 2-chloro-3,4-dimethoxybenzaldehyde (1)

To a solution of 2-chloro-3-hydroxy-4-methoxybenzaldehyde in N,N-dimethylformamide/water, solid potassium carbonate and dimethyl sulfate are added. After heating for a further hour, the solution is cooled and poured into water. The product is separated by filtration and washed with water. The wet product may be dried or used directly in step 6 below. Average yield without purification, 96%.

Step 3. Preparation of 1-(4-methoxyphenyl)-2-nitroethanol

To a cooled solution of nitromethane in methanol is added 4-methoxybenzaldehyde. Sodium methoxide solution is then added slowly with stirring keeping the temperature below 20° C. A thick, white slurry of the nitronate salt is formed which is stirred for a further two hours at a temperature between 10° and 20° C. The mixture is acidified with acetic acid, and methylene chloride and distilled water are added. The product is extracted into the methylene chloride layer, washed with water, and the aqueous layer discarded. The methylene chloride is distilled off under vacuum. The resulting reddish-orange oil is ready for use in the next step. Average yield, 75%.

Step 4. Preparation of 1-(4-methoxyphenyl)-2-aminoethanol acetate

A solution of the nitroethanol in methanol is treated with glacial acetic acid and a slurry of 5% palladium-on-charcoal in methanol. The sealed reaction vessel is pressurized to a low pressure with hydrogen and agitated vigorously. The temperature of the reaction mixture is kept below 60° C. When the hydrogen uptake is complete, the reaction vessel is cooled to 20°–30° C. and the catalyst filtered off. After distilling off the methanol under reduced pressure, the residue is redissolved in ethyl acetate and the volume of solution reduced by distillation under vacuum. The precipitate is spun dry, washed with ethyl acetate and then dried at approximately 40° C. Average yield, 70%.

Step 5. Preparation of 1-(4-methoxyphenyl)-2-aminoethanol (5)

Method A

A suspension of the acetate in methylene chloride is treated with aqueous sodium hydroxide until the pH of the water layer is greater than 9.5. The layers are separated and the methylene chloride layer washed with 10% aqueous sodium hydroxide. The methylene chloride is distilled, then replaced with toluene. Upon complete removal of the methylene chloride the toluene is allowed to cool. The precipitate formed is isolated by filtration, washed with toluene followed by pet ether, and vacuum dried. This free base is suitable for use in the condensation step hereafter described. Average yield, 93%.

Method B

To a suspension of methanol-washed Amberlite IRA-400 resin in methanol is added a methanol solution of 1-(4-methoxyphenyl)-2-amino ethanol acetate. The slurry is stirred at 10° to 20° C. for about an hour and filtered to remove the resin. The methanol filtrate is filtered and concentrated. The concentrate is suitable for use in the condensation.

Step 6. Preparation of 2-chloro-3,4-dimethoxyphenylacetaldehyde (4)

To a stirred solution of methylene chloride, 2-chloro-3,4-dimethoxy benzaldehyde from above and excess methyl chloroacetate at −20° C., is added 25% methanolic sodium methoxide. The reaction is stirred at −10° C. to 20° C. for three hours, then 50% aqueous sodium hydroxide is added over 1.5 hours. After an additional 30 minutes, de-ionized water is added. The pH is adjusted to approximately 5.0 by the addition of 6N hydrochloric acid. The pH is maintained at approximately 5.0 by addition of hydrochloric acid as needed. The reaction is stirred for two to four hours at 30°-35° C. The reaction mixture is allowed to settle, then the aqueous layer separated and re-extracted with methylene chloride. The combined methylene chloride extracts are washed with water, sodium bicarbonate, and again with water. The methylene chloride is removed from the organic extract at reduced pressure and replaced with methanol. This methanolic solution of the acetaldehyde is suitable for use in the condensation step.

Step 7. Preparation of N-[2-hydroxy-2-(4'-methoxyphenyl)ethyl]-2-(2-chloro-3,4-dimethoxyphenyl)ethylamine (7)

Method A

The methanolic solutions of the acetaldehyde from Step 6 and the aminoethanol from Step 5 are mixed and stirred at 0° C. one hour. Sodium borohydride is added in small portions and the temperature maintained below 10° C. The mixture is stirred and allowed to warm to 24° C. over six hours. The reaction mixture is cooled to 15° C. and filtered to give (7) as a white solid. Average yield from the benzaldehyde (1), 55%.

Method B

The methanol solution of 1-(4-methoxyphenyl)-2-aminoethanol from step 5 and 2-chloro-3,4-dimethoxyphenylacetaldehyde from step 6 are cooled to about 10° C. and treated with sodium borohydride. The reaction is stirred four to six hours. The methanol is removed under vacuum. The reaction product is acidified and extracted into methylene chloride. The methylene chloride solution is washed with base and concentrated. The concentrate is treated with ethyl acetate and the product isolated as a white solid suitable for use in step 8.

Step 8. Preparation of 6-chloro-7,8-dimethoxy-1-(4'-methoxyphenyl)-2,3,4,5-tetrahydro-1H-3-benzazepine hydrobromide Method A A solution of 7 is stirred for one hour in a cooled solution of 98% methanesulfonic acid in methylene chloride. Deionized water is added, then the mixture neutralized by slowly adding concentrated ammonium hydroxide solution until the pH reaches 9.0, taking care that the temperature does not exceed 25° C. The aqueous layer is separated and discarded. The methylene chloride solution is washed with distilled water, then distilled off. The residue is dissolved in ethyl acetate, cooled, and hydrogen bromide passed into the solution keeping the temperature between 10° and 20° C. The solution is stirred overnight at 5°-10° and the hydrobromide salt separated by centrifugation, washed with cold ethyl acetate and dried at 55° C. to give the titled product.

B. Chemical requirements for 50 gallon reaction run of the described steps:

| Chemical | Quantity |
| --- | --- |
| (1) methylene chloride | 75 L |
| (2) 2-chloro-3,4-dimethoxybenzaldehyde | 15 Kg (75 g-moles) |
| (3) methyl chloroacetate | 11.25 Kg (106 g-moles) |
| (4) sodium methylate solution (25%) | 18.75 L; 17.7 Kg (82 g-moles) |
| (5) liquid caustic soda (50%) | 8.0 Kg |

-continued

| Chemical | Quantity |
| --- | --- |
| (6) methylene chloride | 20 L |
| (7) water, deionized | 4.8 L |
| (8) hydrochloric acid (18%) | 13.1 L, (more if required to pH 5) |
| (9) methylene chloride, and water, first aqueous extract | 20 L methylene chloride 10 L water |
| (10) methylene chloride, second aqueous extract | 20 L |
| (11) water, deionized first backwash | 20 L |
| (12) sodium bicarbonate solution (6%), second backwash | 1.1 Kg bicarbonate 19 L water |
| (13) water, deionized, final backwash | 20 L |
| (14) methanol | 48 L |
| (15) methanol | 90 L |
| (16) 1-(4-methoxyphenyl)-2-aminoethanol | to be determined as 35 mole % over the acetaldehyde |
| (17) sodium borohydride | 1.2 Kg |
| (18) methanol | 40 L |

EXAMPLE 2

Structure of the Oxazolidine Intermediate

A solution of 2-(4-methoxyphenyl)-1-amino ethanol (0.334 g, 0.02 mole) in 2 mL $CDCl_3$ was added to a solution of 2-chloro-3,4-dimethoxyphenylacetaldehyde (0.428 g, 0.02 mole) in 2 mL of $CDCl_3$. The $CDCl_3$ solution was dried over magnesium sulfate and filtered. Spectral data were obtained by both proton NMR and carbon NMR methods. The chloroform solutions were diluted with methanol and treated with sodium borohydride and filtered to give the secondary amine (7) in a 60% yield.

The 360 MHz proton nuclear magnetic resonance spectrum of the product demonstrated two sets of doublets between 4.8-4.9 ppm which integrate for two protons. This, with the lack at imine proton resonance at 7-9 ppm, is determinative of the structure of the intermediate. A $C_{13}$ nuclear magnetic resonance spectrum shows an equal mixture of cis and trans-isomers.

EXAMPLE 3

Use of a Phase Transfer Agent

To a stirred solution of 2-chloro-3,4-dimethoxy benzaldehyde (800 g, 4 mole) and methyl chloroacetate (640 g, 5.9 mole) in 4 L of methylene chloride at −20° C. was added 25% sodium methoxide (1.0 L, 4.4 mole). The reaction was stirred between 5°-15° C. for 2½ hours and 50% sodium hydroxide (480 g) was added over 1 hour. After an additional ½ hours, water (250 mL) was added and the pH adjusted to 5 with 20% hydrochloric acid. The pH was maintained at 5 by slowly adding additional hydrochloric acid solution for 3 hours at 30°-35° C. The reaction was allowed to settle. The aqueous layer was separated and re-extracted with methylene chloride. The combined methylene chloride extracts were washed with 1.5 L of water. The methylene chloride layer was washed with 1.2 L of 5% sodium carbonate solution with 6.4 g of ethyltriphenylphosphonium iodide added to break the emulsion. The methylene chloride was washed with 1.5 L of water with an additional 6.4 g of ethyltriphenylphosphonium iodide added to break the emulsion. The methylene chloride was removed under reduced pressure and replaced with methanol. The methanol solution was added to 1-(4-methoxyphenyl)-2 aminoethanol (850 g, 5.0 mole) in 8 L of methanol at 0° C. After stirring for 1 hr, sodium borohydride (120 g, 3.24 mole) was added carefully. The reaction was stirred for 6 hrs, cooled, and filtered to give 841 g of N-[2-hydroxy-2-(4'-methoxyphenyl)ethyl]-2-(2-chloro-3,4-dimethoxyphenyl)ethyl amine as a white solid. Assay 99.9%.

What is claimed is:

1. A process for preparing a compound of formula (1):

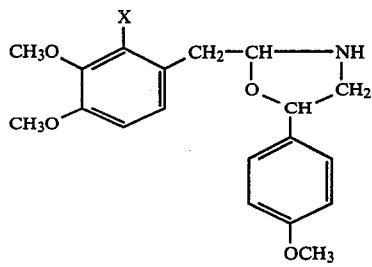 (1)

in which X is chloro or fluoro, that comprises:

(i) reacting a compound of formula (2):

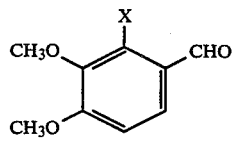 (2)

in which X is chloro or fluoro, with an excess of α-halo lower alkyl alkanoate in the presence of an alkali metal $C_{1-4}$ alkoxide dissolved in a homogeneous solvent system of methylene chloride-methanol at a temperature selected from the range of $-25°$ C. to 50° C. to give a glycidic acid ester;

(ii) treating the glycidic acid ester with aqueous base to produce a glycidic acid that, after decarboxylation and rearrangement, gives a compound of formula (3):

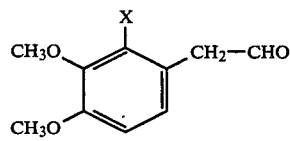 (3)

in which X is chloro or fluoro; and (iii) reacting the formula (3) compound with an excess of a compound of formula (4):

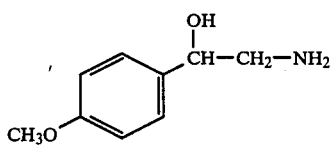 (4)

to form a formula (1) compound.

2. The process of claim 1 in which X is chloro.

3. The process of claim 1 in which a phase transfer catalyst is added to the reaction of steps (i) or (ii) to minimize emulsion formulation.

4. The process of claim 1 in which the mole ratio of the formula (4) compound to the formula (3) compound is about 1.4 to 1.

* * * * *